US00PP21465P3

(12) United States Plant Patent
Westhoff

(10) Patent No.: US PP21,465 P3
(45) Date of Patent: Nov. 9, 2010

(54) **VARIETY OF *CALIBRACHOA* PLANT NAMED 'WESCADOPI'**

(50) Latin Name: *Calibrachoa*
Varietal Denomination: Wescadopi

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 12/383,757

(22) Filed: Mar. 26, 2009

(65) Prior Publication Data

US 2010/0251448 P1 Sep. 30, 2010

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP18,694 P2 * 4/2008 Klemm ..... Plt./413

* cited by examiner

*Primary Examiner*—June Hwu
(74) *Attorney, Agent, or Firm*—The Webb Law Firm

(57) ABSTRACT

A new and distinct *Calibrachoa* plant named 'Wescadopi' that exhibits double-flowers and a compact growth habit.

2 Drawing Sheets

Botanical classification: *Calibrachoa.*
Varietal denomination: 'Wescadopi'.

BACKGROUND OF THE INVENTION

The present invention comprises a new and distinct cultivar of *Calibrachoa* known by the varietal name 'Wescadopi'. The new variety was discovered in Siidlohn, Germany in August of 2007. The new variety has been vegetatively asexually reproduced via cuttings, and the first date of asexual reproduction was in 2007/2008 in Siidlohn, Germany. The new variety is the result of a planned breeding program cross between unpatented *Calibrachoa* plant MiniFamous Double Pink (female parent) and unpatented *Calibrachoa* plant Seedling 06P942 (male parent). The purpose of the breeding program was to develop a double-flowering *Calibrachoa* variety. The new variety exhibits similar flower color and shape with its female parent, but exhibits smaller flowers and more compact plants than both parents. 'Wescadopi' exhibits a similar foliage color, flower bud size, and its double-flowering characteristic with *Calibrachoa* plant 'MiniFamous Double Dark Pink', (unpatented), but the new variety has smaller flowers that are lighter pink in color, less filled and unveined flowers, and smaller leaves (3.2×0.7 cm vs. 4.0×1.1 cm) when compared to 'MiniFamous Double Dark Pink'. Further, the new variety differs from 'MiniFamous Double Dark Pink' because it has 5 petals inside the calyx, while 'MiniFamous Double Dark Pink' has 10-14 petals inside the calyx. The new variety has been trial and field tested and has been found to retain its distinctive characteristics and remain true to type through successive propagations. The following characteristics also distinguish 'Wescadopi' from other *Calibrachoa* varieties known to the breeder:

1. Compact growth habit;
2. Double-flowering pink flowers;
3. Elliptic-shaped and small-sized leaves;
4. Small-sized flowers without veins; and
5. Contrasting foliage and flower colors.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
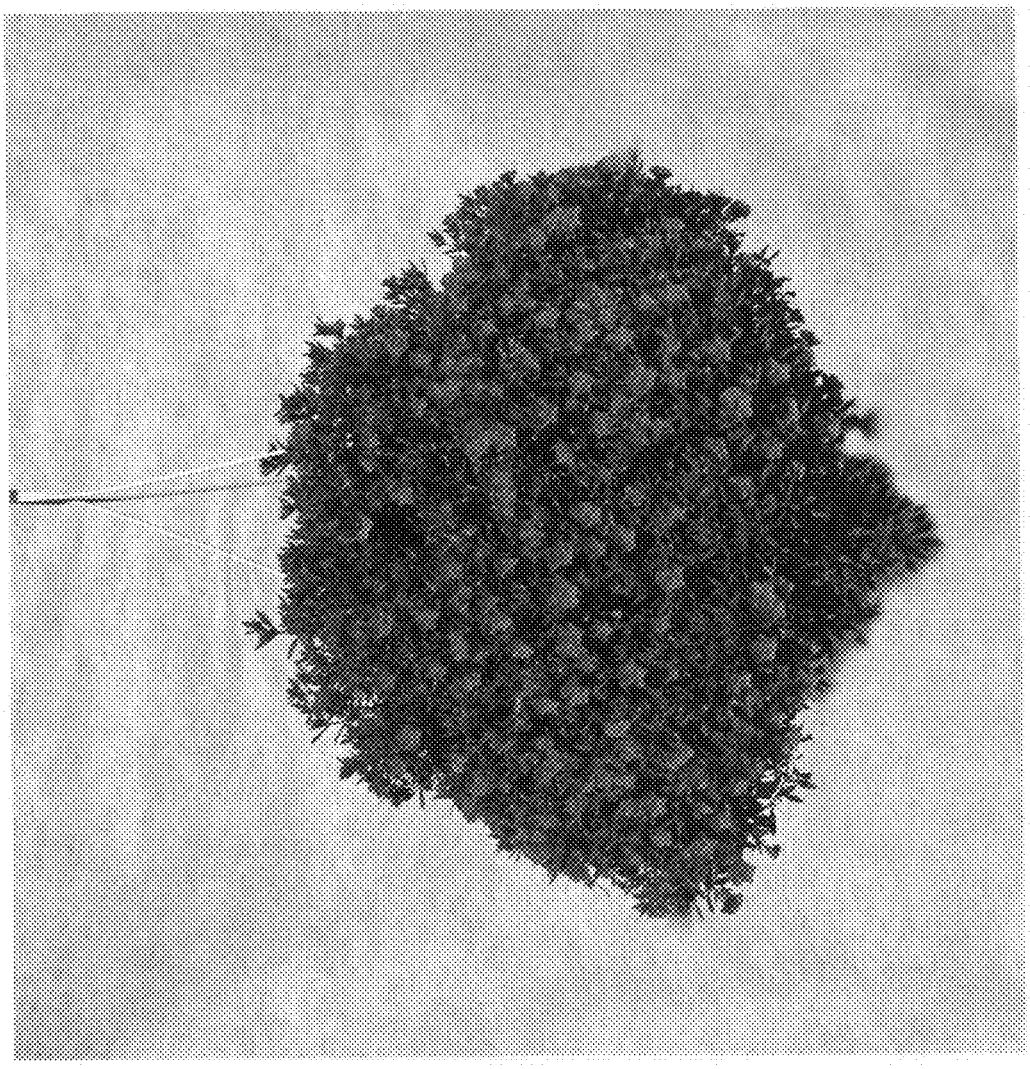
FIG. 1 is a view of an entire plant of the new variety.
Figure 2:
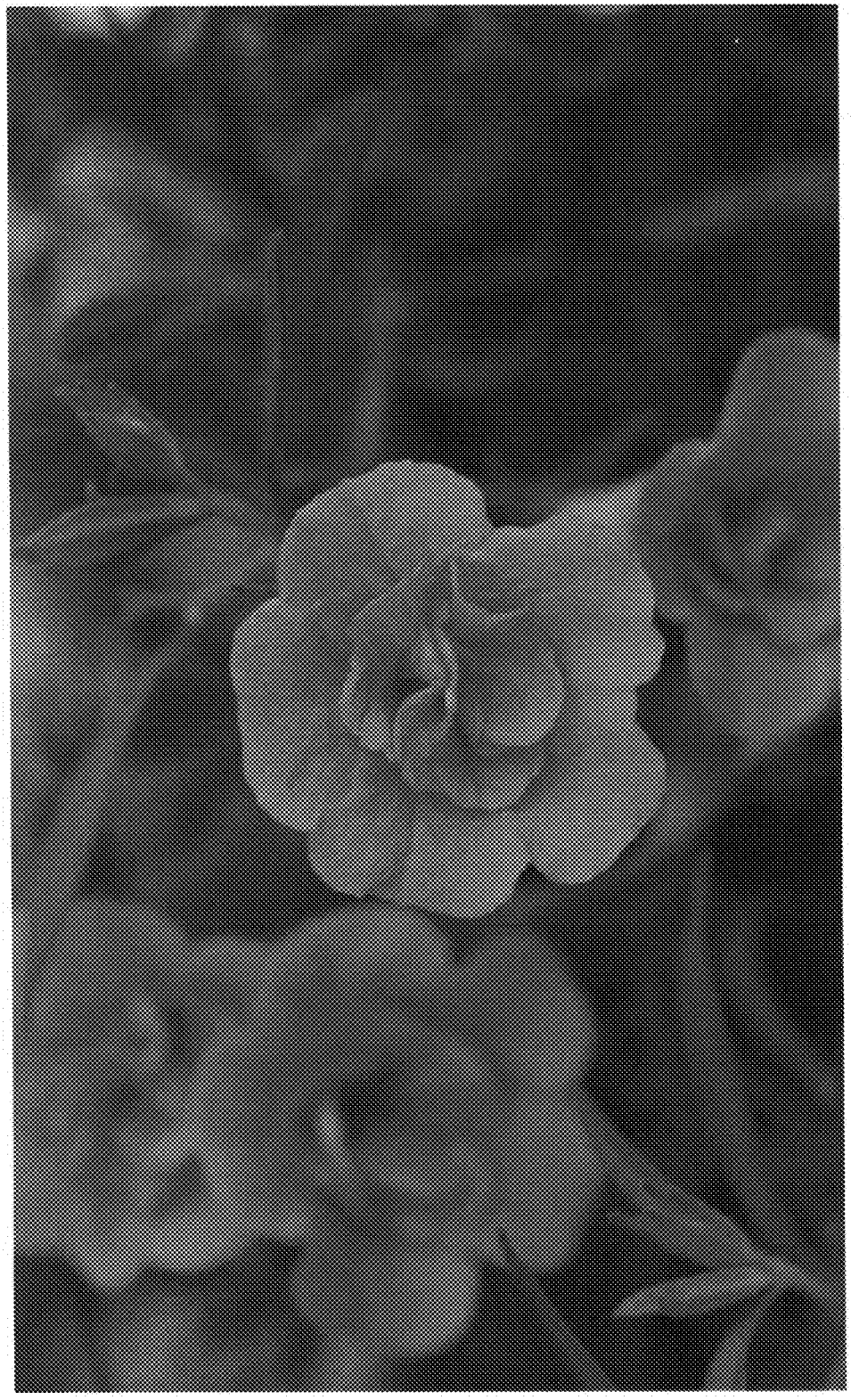
FIG. 2 is close-up photograph of a flower of the new variety.

The following detailed description sets forth the characteristics of 25 week old 'Wescadopi' plants grown inside a greenhouse in 12 cm pots and baskets in Siidlohn, Germany. The average day temperature was 20-25° C., and the average night temperature was 16-18° C. The color readings were taken indoors under natural light. Color references are primarily to The 2001 R.H.S. Colour Chart of The Royal Horticultural Society of London.

PLANT

Time to initiate roots: 10-14 days at about 20° C.
Time to develop roots: 21 days at about 20° C.
Rooting habit: Fine, fibrous, and well-branched.
Root color: 158A.
Form: Compact and spherical.
Branching habit: Very good; at the base and every node.
Height (from soil to top of flowers):
*Pot grown plants.*—12-15 cm.
*Basket grown plants.*—24 cm.
Plant diameter: 45-52 cm.
Vigor: Very strong.
Lateral branches:
*Form.*—Compact and spherical.
*Color.*—144A.
*Texture.*—Dull, short pubescence.
*Diameter.*—About 1.0 mm.

*Internode length.*—About 0.6-1.5 cm.
*Quantity.*—At every node.

Foliage:
*Arrangement.*—Alternate and single.
*Number of leaves per branch.*—Plentiful; approximately 70-90 leaves per branch.
*Size of leaf.*—Length: About 3.2 cm. Width: About 0.7 cm.
*Shape of leaf.*—Narrow and elliptic.
*Shape of apex.*—Acute.
*Shape of base.*—Attenuate.
*Texture* (*upper and lower leaf surfaces*).—Dull.
*Aspect.*—Flat.
*Margin description.*—Entire.
*Color.*—Young leaves: Upper surface: 146A. Lower surface: 146B. Mature leaves: Upper surface: 147A. Lower surface: 147B.
*Petiole.*—Not applicable, leaves taper to the petiole.
*Veins.*—Color: Upper surface: 147B. Lower surface: 147C.

FLOWER

Natural flowering season: From April to the end of autumn in Germany.

Flower type and habit: Single flowers near the top of branches.

Number of flowers per plant: Numerous; approximately 30-50 flowers per plant and 3-4 opened flowers per branch when grown in a 12 cm pot.

Flower description: Five petals are fused and form a usual *Calibrachoa* corolla. In the center of the corolla (the throat), the stamens are transformed into petals. The new variety has 5 small petals in the center that form a filled double flower.

Corolla:
*Diameter.*—About 2.3 cm.
*Flower tube length: About.*—1.5 cm.
*Flower tube diameter at distal end.*—About 0.63 cm.
*Flower tube diameter at proximal end.*—About 2.5 mm.
*Petal length from throat.*—Corolla petals: About 0.9 cm. Inner petals: About 0.38 cm.
*Petal width.*—Corolla petals: About 1.2 cm. Inner petals: About 1.0 cm.
*Petal quantity.*—Corolla petals: Five petals fused. Inner petals: Filled with 5 small petals.
*Petal apex shape.*—Corolla petals: Obtuse. Inner petals: Emarginate.
*Texture* (*upper and lower leaf surfaces*).—Smooth.
*Color.*—When opening: Upper surface: N74A. Lower surface: N74C. Fully opened: Upper surface: N74B. Lower surface: 75A to 75B. Flower throat (inside): 8A to 8D. Flower throat, vein: 166A. Flower tube (outside): 160C. Flower tube, vein: 166A. Petal color, fading to: N74B.

Peduncle:
*Length.*—About 1.0 cm.
*Diameter.*—About 0.9 mm.
*Color.*—144A.
*Orientation.*—Acutely angled, holding all flowers outwards in optimum positions.
*Strength.*—Flexible.

Bud:
*Shape.*—Oblanceolate.
*Length.*—About 1.5 cm.
*Diameter.*—About 0.4 cm.
*Color.*—Base: 145C. Middle: 145C. Tip: 77C to 77D.

Calyx:
*Description.*—Salverform, filled calyx with double-flowering.
*Length.*—About 2.3 cm.
*Diameter.*—About 2.3 cm.
*Sepal shape.*—Five lanceolate-shaped (3 long, 2 short) sepals fused at the base.
*Sepal margin.*—Entire.
*Sepal texture* (*upper and lower leaf surfaces*).—Dull, pubescence present.
*Sepal color.*—Upper surface: 147B. Lower surface: 147B.

Disease resistance: None observed to date.

Fragrance: None.

Weather tolerance: Good.

Lasting quality: Long lasting; 8-14 days, depending on environmental conditions.

Seed production: None observed to date.

REPRODUCTIVE ORGANS

Stamens: Absent because stamens transformed to petals.

Pistils:
*Number.*—One to three.
*Length.*—About 7.0 mm.
*Styles.*—Length: About 4.5 to 5.0 mm. Color: 144D.
*Stigma.*—Shape: Ovate. Color: 144A. Ovary color: 144C.

I claim:

1. A new and distinct variety of *Calibrachoa* plant named 'Wescadopi' substantially as shown and described herein.

* * * * *

UNITED STATES PATENT AND TRADEMARK OFFICE

CERTIFICATE OF CORRECTION

PATENT NO. : PP21,465 P3
APPLICATION NO. : 12/383757
DATED : November 9, 2010
INVENTOR(S) : Westhoff It is certified that error appears in the above-identified patent and that said Letters Patent is hereby corrected as shown below:

Column 1, Line 8, and Column 2, Line 14, "Siidlohn, Germany" should read -- Südlohn, Germany --

Signed and Sealed this
Twelfth Day of April, 2011

David J. Kappos

David J. Kappos
*Director of the United States Patent and Trademark Office*